United States Patent
Ramirez Sabag et al.

(10) Patent No.: US 11,613,988 B2
(45) Date of Patent: Mar. 28, 2023

(54) RADIOCHEMICAL AND CHROMATOGRAPHIC ANALYSIS SYSTEM OF TRACERS, IN SITU AND IN REAL TIME

(71) Applicant: INSTITUTO MEXICANO DEL PETROLEO, Mexico City (MX)

(72) Inventors: Jetzabeth Ramirez Sabag, Mexico City (MX); Jose Francisco Trejo Reyes, Mexico City (MX)

(73) Assignee: INSTITUTO MEXICANO DEL PETROLEO, Mexico City (MX)

(*) Notice: Subject to any disclaimer, the term of this patent is extended or adjusted under 35 U.S.C. 154(b) by 293 days.

(21) Appl. No.: 17/091,555

(22) Filed: Nov. 6, 2020

(65) Prior Publication Data
US 2021/0140315 A1     May 13, 2021

(30) Foreign Application Priority Data
Nov. 8, 2019 (MX) .................. MX/A/2019/013353

(51) Int. Cl.
    *E21B 47/11*     (2012.01)
    *G01N 33/28*     (2006.01)
    *G01N 30/14*     (2006.01)
    *E21B 47/12*     (2012.01)
    *G01N 30/00*     (2006.01)

(52) U.S. Cl.
    CPC .............. *E21B 47/11* (2020.05); *E21B 47/12* (2013.01); *G01N 30/14* (2013.01); *G01N 33/2823* (2013.01); *G01N 2030/0095* (2013.01)

(58) Field of Classification Search
CPC ......... E21B 47/11; E21B 47/12; G01N 30/14; G01N 33/2823; G01N 2030/0095
See application file for complete search history.

(56) References Cited

U.S. PATENT DOCUMENTS

| | | | | |
|---|---|---|---|---|
| 3,902,362 A | * | 9/1975 | Tomich ................. | G01V 9/00 166/250.01 |
| 4,782,898 A | * | 11/1988 | Wellington ........... | E21B 47/111 436/27 |
| 5,256,572 A | * | 10/1993 | Tang ...................... | E21B 47/11 436/27 |
| 6,290,284 B1 | * | 9/2001 | Crean .................... | B60P 3/34 296/168 |
| 7,985,382 B1 | * | 7/2011 | Henry .................... | E04H 1/1277 422/291 |
| 9,835,024 B2 | * | 12/2017 | Ramirez Sabag ...... | E21B 47/11 |

* cited by examiner

*Primary Examiner* — David P Porta
*Assistant Examiner* — Jeremy S Valentiner
(74) *Attorney, Agent, or Firm* — FisherBroyles, LLP; Jason P. Mueller

(57) ABSTRACT

The present invention considers bringing a mobile unit closer to the site of interest and conduct the quantification of the tracers by performing the detection methods in situ and in real time at the wellhead, and that can be moved to the site on numerous occasions for the preparation of results during the test where the quantification of tracers is necessary, helping to speed up and reduce times that, until now, have not been achieved with stationary laboratories and that depending on the laboratory can last up to three months providing results.

12 Claims, 7 Drawing Sheets

RADIOCHEMICAL AND CHROMATOGRAPHIC ANALYSIS SYSTEM OF TRACERS, IN SITU AND IN REAL TIME

This application claims priority to Mexico Patent Application No. MX/a/2019/013353, filed Nov. 8, 2019, the entire contents of which are incorporated herein by reference.

FIELD OF THE INVENTION

The present invention solves the problem of timely measurement and on the location of wells involved in tracer testing applications in reservoirs (both radioactive and chemical), and consists of an innovative mobile radiochemical and chromatographic analysis system, for both types of tracers in real time, being constituted in physical form by two joined vehicles, the motor vehicle and its trailer.

BACKGROUND OF THE INVENTION

Most of the deposits in the world are in a second phase of exploitation, in which it is necessary to know the heterogeneities of the reservoir and how they influence the hydrocarbon recovery processes. Tracer tests in reservoirs constitute a technique that allows determining flow characteristics of the porous medium, as well as the residual saturation/remaining oil, which is why they have gained importance in recent years. The main stages of reservoir layout studies are as follows: design, implementation (execution), and interpretation.

SUMMARY OF THE INVENTION

The present invention has a strong impact on the execution stage (it is more effective and efficient) and additionally, the benefit of having a reliable tracer response in the interpretation stage, since the results of the study will more faithfully reflect what happens in the porous medium. One of the great problems of tracer testing is related to the operational part, a phase in which it is necessary to measure the concentration of the compounds of interest produced in the fluids of the producing wells. The way in which both types of tracers (radioactive and chemical) are conventionally measured is in a stationary laboratory, and most likely in a laboratory that detects and quantifies chemical tracers, and another laboratory to detect and quantify radioactive tracers, due to the nature of them. For samples analysis, these are transferred from the point of extraction or collection to the laboratory. Once they arrive at the destination, the conditions in which they are received are not necessarily the conditions under which they were collected, and they frequently present packaging problems and delays in response time for results. In such circumstances, it is extremely important to consider the time it takes for the samples to arrive at the laboratory for analysis, because the fluid or fluids contained may continue to react in the sample and generate physical or chemical changes, causing alterations in the results.

The present invention provides a system of equipment installed on a mobile structure that allows access to the well location. Therefore, one of the objects of the present invention is to obtain more representative data on concentrations of tracers, both radioactive and chemical, in order to accurately obtain what happens in the reservoir being studied. This avoids the reaction of the sample that occurs while it is transferred to a fixed laboratory for analysis. Another object is the time of determination of the components of the sample in real time; likewise, the samples are analyzed continuously, thereby ensuring that the analysis of the samples is reliable and statistically representative. Similarly, another object of the present invention is to provide a real-time, on-line measurement process for the concentration of gamma emission radioactive tracers. All of the above allows us to have statistically representative data, and with it, the possibility of obtaining as a result of the interpretation of the test, the valuable information that is expected from this type of study.

In view of what is known to the applicant, there is no precedent for measuring concentrations of chemical and radioactive tracers in the location of the wells under study. What is done in a conventional way is the acquisition of samples of the fluids produced on the surface and send them to the fixed laboratories for analysis, which represents uncertainty in the results, since when dealing with chemical tracers, even when preserved samples at 4 C, there is always risk of a reaction inside the sample holder if they are not analyzed within 6 hours of being collected. Thus, the fact of measuring the sample before one hour of its acquisition, as is the case of the present invention, significantly reduces the uncertainty in this regard, since what is obtained in the chromatograph will be practically the measurement that faithfully reflects the conditions of the sample. This is how the sample of the fluids produced in the well under study was collected. Another strength of the present invention is the sensitivity of the results. Obtaining 100% reliable results with opportunity, allows decision making at the moment, based on the results that are being obtained, in such a way that it significantly reduces costs, and problems that frequently occur in this type of tests may be avoided, as well as, the possibility of modifying the sampling or perhaps the expenses, duration of the test, etc., in order to obtain the expected results.

Additionally, a very relevant advantage of the present invention, over conventional analysis, is the precision of the results; and furthermore, the timeliness of them. It goes without saying that having the capabilities to detect and quantify two types of tracers (radioactive and chemical) on-line and in real time is a great technical support, allows the confirmation of various behaviors, in case there are doubts (which in fact, typically there are).

Next, we describe the advantages of radioactive tracer detection and quantification methods over conventional methods:

- Measures concentration of 3 radioactive gamma emission tracers ($^{57}Co$, $^{192}Ir$ and $^{60}Co$) in the well discharge line, in real time and practically continuously.
- Does not require sampling to obtain the tracer response curve.
- Reports statistically reliable response curves, so it accurately reflects the behavior of the tracer in the reservoir.
- Avoids the cost associated with taking samples for the radiochemical analysis of fluids (occupationally exposed personnel-SOPs, specialized crews, sample carrier cylinders, transportation and laboratory analysis of the samples).
- Guarantees the measurement of the radioactive tracers total production in the study well, since the measurements are practically continuous, simultaneously as the fluid is produced in the well.
- It is self-sufficient in energy consumption (powered by solar energy) during the development of the entire test; as well as the protection of the information continuously (2-6 continuous months).

Transmission of data in real time through its own visualization platform.

Data report (counts per minute, radioactive activity, concentration), in real time.

Real-time communication allows concentrations to be calculated and plotted as data is being acquired and recoveries obtained for the corresponding tracer.

The system offers cutting-edge technology with which it is possible to design, execute and interpret totally innovative tracer tests, obtaining additional information of great value for hydrocarbon recovery projects.

It should be noted that, in the patent literature, the invention described in Patent MX298534 is integrated, in which the inventor presents a kit comprising an apparatus necessary for the on-line measurement of radioactive tracers at the head of oil wells. Reference is made to a new technology to measure the activity concentrations of a tracer in real time, using a liquid scintillation radiation detector, with characteristics that make it possible to detect up to three different tracers and be able to operate under conditions of temperature up to 150° C.

BRIEF DESCRIPTION OF THE DRAWINGS

With the purpose of understanding the radiochemical and chromatographic analysis system of tracers, in situ and in real time, object of the present invention, reference will be made to the accompanying drawings. While specific arrangements of accessories and devices with which this invention can be practiced are illustrated, it should not be understood that the invention is limited to any specific arrangement thereof.

DETAILED DESCRIPTION OF THE INVENTION

The present invention refers to an innovative mobile radiochemical and chromatographic analysis system used in the detection and quantification of tracers. In the well discharge line analysis, radioactive tracers are quantified, while chemical tracers are quantified inside the laboratory. Both types of tracers are detected and quantified in real time.

Figure 2:
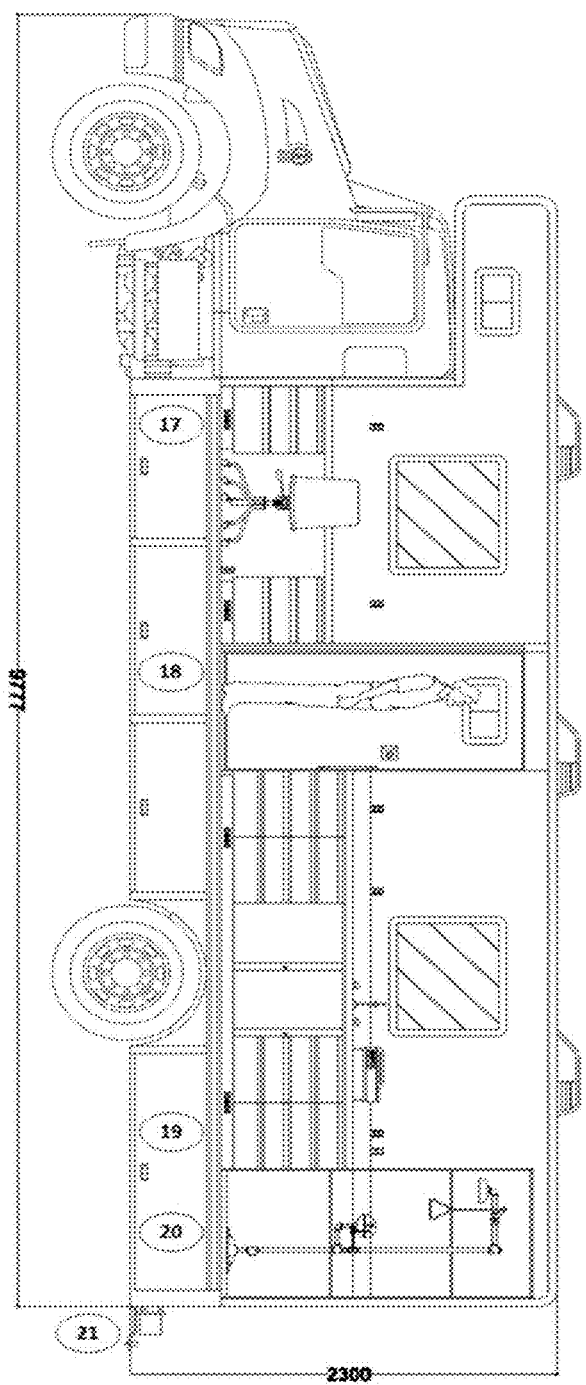
FIG. 2 illustrates the distribution of elements in the radiochemical and chromatographic analysis system of tracers, in situ and in real time, in a right side interior view.
Figure 5:
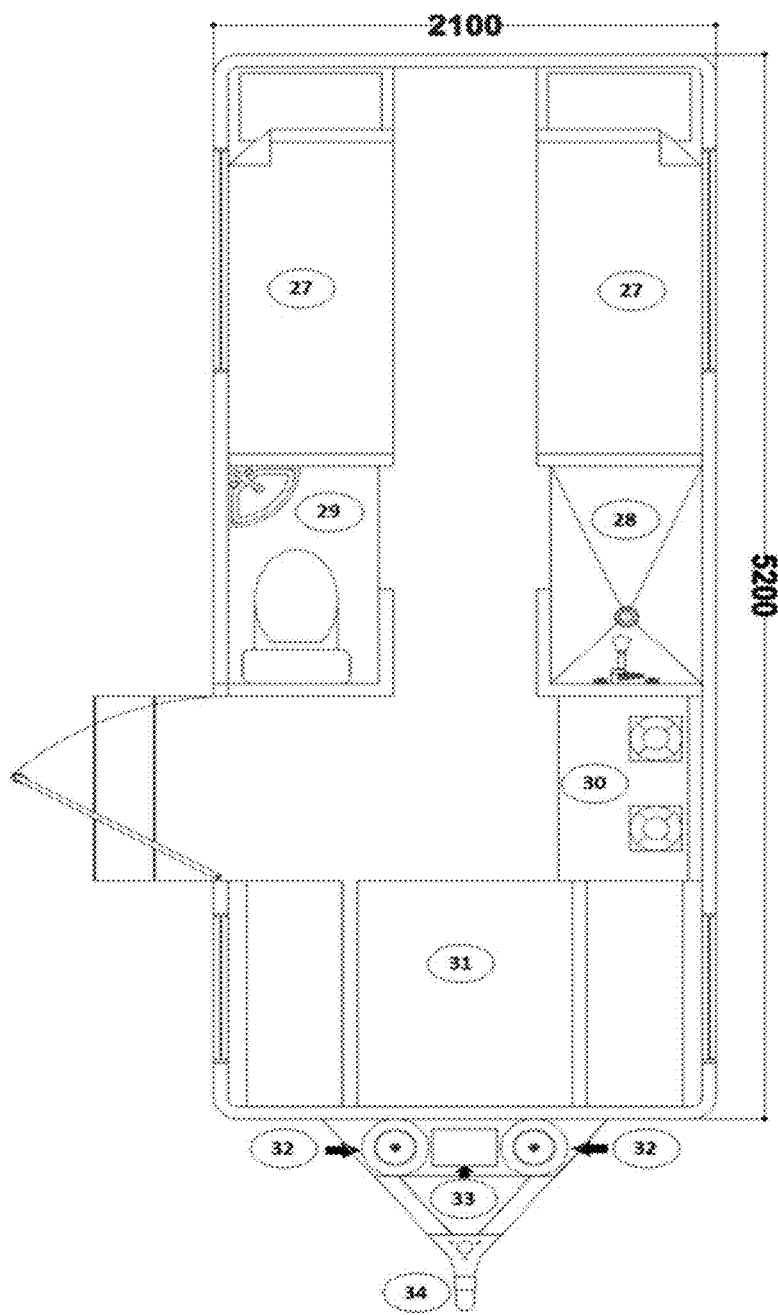
FIG. 5 illustrates the distribution of elements in the sleeping trailer of the radiochemical and chromatographic analysis system of tracers, in situ and in real time of an interior view of the plant.

In a physical way, the present invention is constituted by two linked vehicles, the mobile laboratory with the equipment of the radiochemical and chromatographic analysis system of tracers, in situ and in real time (motor vehicle shown in FIG. 2), and its trailer (FIG. 5), being point 21 of FIG. 2 integrated to point 34 (trailer lance) of FIG. 5 for the assembly of both vehicles.

The radiochemical and chromatographic analysis system of tracers, in situ and in real time, presents the novelty of reaching the site and offering the service of radiochemical and chemical analysis of the compounds of interest used in the tracers tests guarantying superior analyzes that the ones carried out in fixed laboratories, especially considering the opportunity in the results and in the conservation of the samples from the wells. This system allows to shape the response curves of the tracers involved in the different applications of reservoir layout studies. It is characterized by the fact that the graph of concentration versus time is formed in real time, point by point, for both chemical and radioactive tracers. The present invention is useful for those known in the oil industry as tracer tests, either for formation characterization purposes (typically interwell tests), residual saturation/oil carryover (single well tracer tests), or also, to estimate the width and depth of the fractures caused in the stimulation process of the wells. Likewise, it is highlighted that this system uses certain recently developed tools (one of a kind), such as the on-line measurement system of radioactive tracers at the head of oil wells, which is used for on-line measurement of radioactive tracers.

Therefore, it is very convenient to have in situ radioactive or physicochemical analysis, that is, the concentration of the tracers, object of this type of study, contained in the fluids produced in the wells involved in the aforementioned tests; in order to have the detection and quantification of the compounds of interest (radioactive and/or chemical) from the tracer tests either between wells and from a single well.

The real-time, in situ, radiochemical and chromatographic analysis system uses a visibly named vehicle specifically designed to detect and quantify the two types of tracers in situ and in real time.

Figure 1:
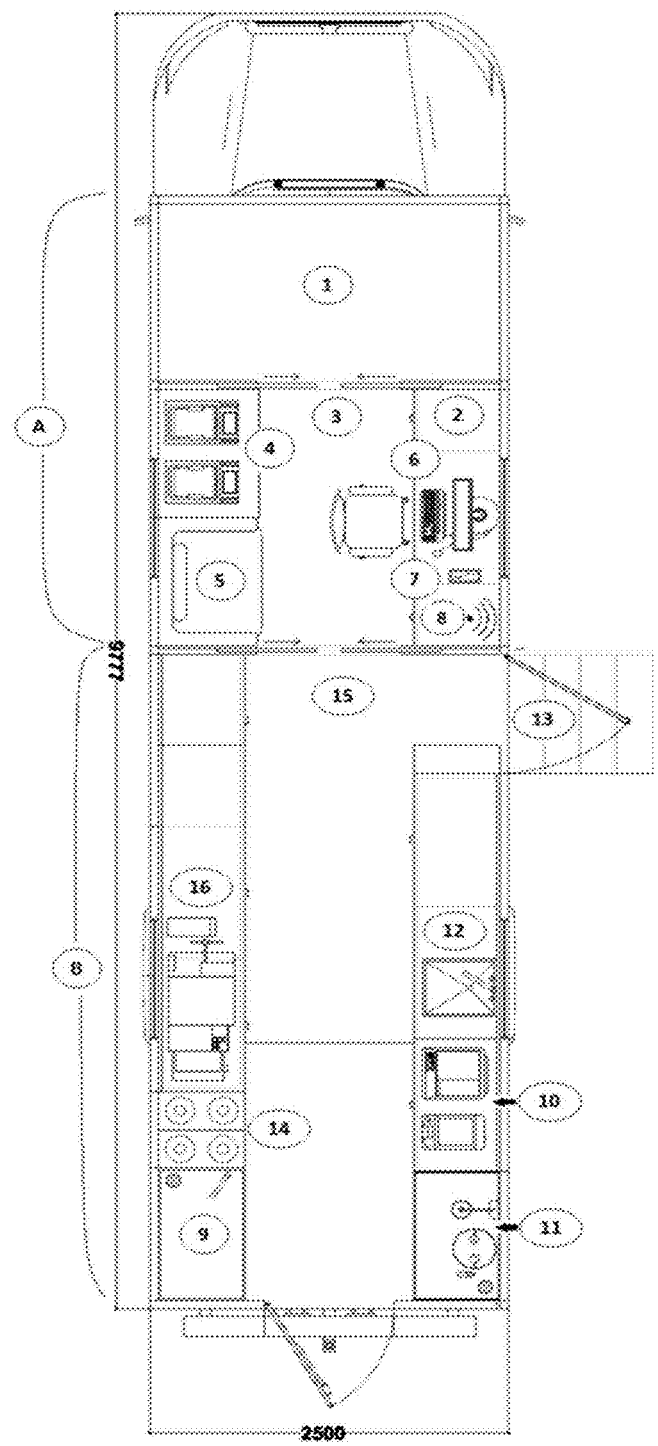
FIG. 1 illustrates the distribution of the mobile laboratory with the equipment of the radiochemical and tracer chromatographic analysis system, in situ and in real time. The distribution of the elements is observed in detail in an interior plan view.

In accordance with FIG. 1, the tracer, in situ and real-time radiochemical and chromatographic analysis system is divided into two large parts; section A and B. Each of them is intended for the tracer analysis processes, being radioactive tracers in section A and chemical tracers in section B. To carry out the complete development of the sub-processes, all the equipment located in the radiochemical and tracer chromatographic analysis system in situ and in real time is necessary.

Section A involves the following equipment, furniture, and accessories: 1.—Bedroom or warehouse cap, storage space and equipment warehouse in the tracer radiochemical and chromatographic analysis system, in situ and in real time; 2.—desk with two drawers, furniture occupied to carry out various tasks in the development of the tracer analysis; 3.—computer room, which includes computer equipment with the necessary software to carry out the analysis of the results obtained from the radioactive tracers in the well; 4.—scales with a cap, measuring equipment used to quantify components used in sub-processes: 5.—armchair, rest furniture; 6.—On-line measurement system of radioactive tracers at the head of oil wells, equipment used to obtain the pertinent data of the tracers injected into the well; 7.—oscilloscope, electronic equipment used for the analysis in the derivative sub-processes of processes A and B; 8.—Wireless communication equipment, used to receive information from the radioactive tracers on-line measurement system at the head of oil wells, which will later be sent to the computer equipment for analysis.

Section B involves the following equipment, furniture and accessories: 9.—fume extraction hood, support equipment to carry out the ventilation of unwanted gases outside the radiochemical and chromatographic analysis system of tracers, in situ and in real time, during the relevant threads; 10.—Centrifuges, support equipment for the separation of phases in the relevant sub-processes; 11.—emergency shower with eyewash, staff support team that works on the radiochemical and chromatographic analysis system of tracers, in situ and in real time, intended for an emergency due to contact with chemical agents that may be harmful to staff: 12.—sink, support equipment for the disposal or handling of liquids used during the sub-processes, 13.—retractable ladder, support equipment to facilitate the entry of personnel on board the radiochemical and chromatographic analysis system of tracers, in situ and in real time; 14.—gas cylinders, gas containment and storage equipment used in analysis sub-processes in tracers; 15.—work area, space destined for the use of personnel that work in the tracer analysis sub-processes; 16.—chromatograph, equipment used to perform component analysis in sample fluids.

FIG. 2 shows the interior rear face of the radiochemical and chromatographic analysis system of tracers, in situ and in real time, right-side view, where: 17.—main power generator of 12,500 watts; 18.—Trunk for the guard of the radioactive tracers on-line measurement stern at the head of oil wells; 19.—trunk for storing cables and connectors; 20.—trunk for storing supplies; 21.—hitch the trailer, bedrooms. In this same Figure, at point 11, a safety shover is observed in case of emergencies, letter a) represents access to the system. Similarly, in this FIG. 2, the applicant notes that point 21 is the draft for the trailer, bedrooms, which is assembled with point 34 (lance) of FIG. 5, this integration being, as a whole, the radiochemical and chromatographic analysis system of tracers, in situ and in real time, constituted in physical form by two joined vehicles, the motor vehicle and its trailer, the latter shown in FIG. 5.

Figure 3:
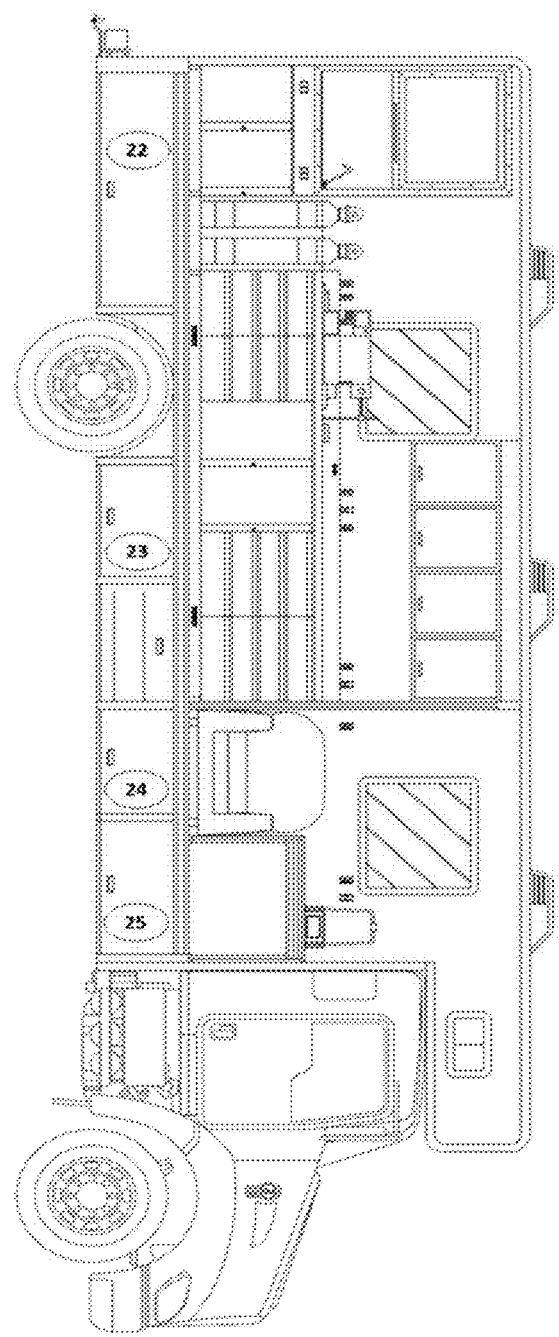
FIG. 3 illustrates a schematic view of the inside of the radiochemical and chromatographic analysis system for tracers, in situ and in real time, in a left side view.
Figure 4:
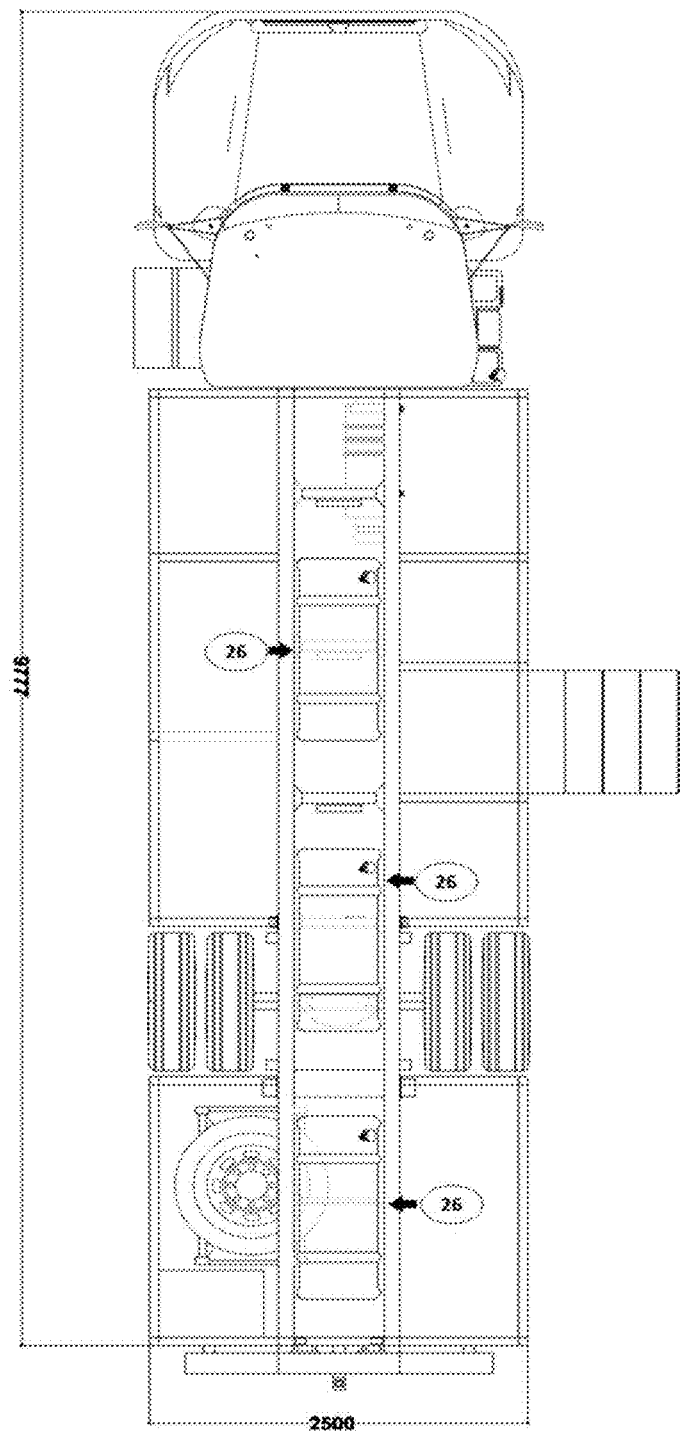
FIG. 4 illustrates the distribution of elements in the tracer radiochemical and chromatographic analysis system, in situ and in real time from a plan view of the chassis.

FIG. 3 illustrates the exterior left lateral schematic view, interior posterior face, of the radiochemical and chromatographic analysis system of tracer, in situ and in real time, where: point a) represents the access to the radiochemical and chromatographic analysis system of tracers, on site and in real time; item 11.—safety shower in case of emergencies; 16.—represents a gas chromatograph coupled to mass model 7890B; 14.—gas tanks, chromatograph supplies; 9.—extraction hood; 23.—10,000 watt backup power generator; likewise, the ventilation system is shown in FIG. 4, plant diagram, with point 26.

FIG. 5 shows the distribution of elements in the sleeping trailer of the radiochemical and chromatographic analysis system of tracers, in situ and in real time of an interior view of the plant: 27.—beds; 28.—telephone shower; 29.—sanitary; 30.—table with double grill; 31.—table convertible to bed; and, 32.—10 kg gas tanks; 33.—Generator; and 34.—Lance (it is assembled with point 21 of FIG. 2).

Figure 6:
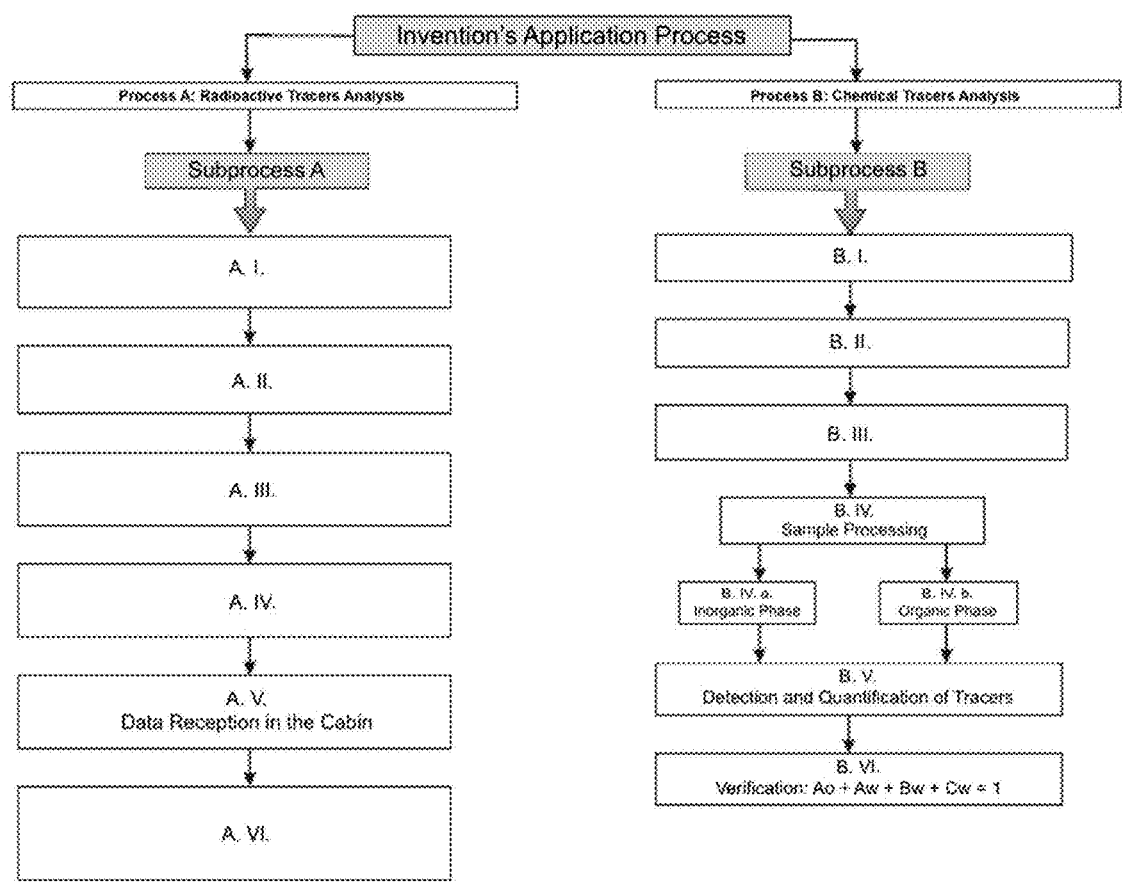
FIG. 6 illustrates the application process of the invention. It is observed that there are two parallel processes in the system, analysis of radioactive tracers (A) and analysis of chemical tracers (B), each of them with its corresponding sub-processes

FIG. 6 shows the application process of the present invention, where there are two parallel processes in the system, analysis of radioactive tracers (A) and analysis of chemical tracers (B), each with its corresponding sub-processes.

The process includes an analytical procedure that generally consists of a liquid-liquid extraction with dichloromethane in two phases (aqueous phase and organic phase). As a result of this procedure, 4 vials are obtained (two from the aqueous phase and two from the organic phase) for subsequent quantification in the gas chromatograph.

It is mentioned that the processes for detecting and quantifying radioactive and chemical tracers are independent and, according to the case study, can be executed in parallel. The following describes the process sequence to illustrate the best way to use the present invention to determine the concentration of both chemical and radioactive tracers:

Process A, Radioactive Tracer Analysis. Thread A:

AI. Assembly of on-line measurement system for radioactive tracers at the head of oil wells. The mechanical system, the feeding system, as well as the electronic system are assembled. In addition, the operation of the assembly of the integral system of the on-line measurement system of radioactive tracers at the head of oil wells is verified.

A. II. Installation of the on-line measurement system in the well (tracer line detection). Coupling of the equipment to the well head and arrangement of the fluid feed lines in the well.

A.III. Verification of the operating pressures of the on-line measurement system for radioactive tracers at the head of oil wells. Verification of the inlet and outlet pressures of the system; verification of non-existence of leaks and implementation of the software for the acquisition and extraction of data from the on-line measurement system for radioactive tracers at the head of oil wells.

A.IV. Start-up and configuration of the on-line measurement system for radioactive tracers at the head of oil wells. System Power Up; implementation tests of the information being transferred; scheduling the equipment according to the test design and commissioning the equipment before the injection of tracers (1 to 2 hours).

A.V. Data reception in the cabin. Monitoring of the measurement inside the Trazamóvil (room A of FIG. 1), once the test monitoring times have concluded, according to the design; wells are closed.

A.VI. Disassembly of the on-line measurement system for radioactive tracers at the head of oil wells. Disassembly of the electronic system, the mechanical system and the power system of the radioactive tracer on-line measurement system at the head of oil wells. Finally, protection of the on-line measurement system for radioactive tracers at the head of oil wells on the side of the Mobile System (number 18 of FIG. 2).

Analytical Method. FIG. 1 Section B shows each of the elements necessary to carry out the chemical tracers analysis process.

The procedure for the detection and quantification method of chemical and analytical tracers is as follows:

Process B, Analysis of Chemical Tracers. Thread B:

BI. Sampling. Obtaining the sample and receiving it in the laboratory.

B.II. Sample preparation. Pour the content required for the analysis (specify 50 or 10 ml, depending on the emulsificaton of the sample) into a cylinder; label and order the required sample along with the remaining content and storage in a container. Choice of type of centrifuge (1 lt or 10 ml capacity), and phase separation.

B.III. Sample storage. Row in samples waiting to be centrifuged and waiting for sample processing.

B. IV. Sample processing.

B.IV. a. Inorganic phase. Carry out a liquid-liquid extraction of the aqueous phase, with a total volume of 10 ml of dichloromethane divided into three sub-extractions. Obtaining the Extract 1. Take a 1.5 ml aliquot for chromatography. Carry out a second liquid-liquid extraction, with a total volume of 10 ml of dichloromethane divided into three sub-extractions. Obtaining the Extract 2. Take a 1.5 ml aliquot for chromatography and line up the chromatograph service (distinguishing the source).

B.IV.b. Organic phase. Sample washing, perform the liquid-liquid extraction, and distribute it in three sub-extractions. Obtain Extract 3, take a 1.5 ml aliquot for chromatography). Wash the remaining sample again, perform liquid-liquid extraction, divide it into three sub-extractions, Obtain Extract 4. Take 1.5 ml aliquots for chromatography and place in a row in the chromatograph service (distinguishing the origin).

B.V. Tracer Detection and Quantification. A mass coupled gas chromatograph model 7890B is used, with the following process: Inject a sample into the gas chromatograph (performed in the injector); separate the sample into individual components (the column used is a DB-WAX column capable of separating the components of interest); detect the compounds that were in the sample (the detector used in the equipment is a flame ionization detector (FID); the detector sends the signal to the computer program where it is possible to visualize each signal in the form of a chromatogram. The chromatographic process lasts 15 min per extract. Therefore, the complete process for the 4 extracts is 45 min. The specific parameters that can be loaded into the equipment software are shown in Table 1, and the heating ramps are established as follows:

B.VI. Check. Verify the results of all the components analyzed, two per organic phase and two per inorganic phase, in the most general case it will be through the following material balance:

i. Balance the sum: Ao+Aw+Bw+Cw=1. As part of the implemented method of real-time measurement.

ii. Incorporate the results to the analysis in an automated way in an on-line system (including the chromatogram of each compound of interest).

EXAMPLE. The following example is presented relating to the radiochemical and chromatographic analysis system of tracers, in situ and in real time, according to an object of the present invention and described above, without limiting its technical scope:

A single-well test of chemical and radioactive tracers is carried out in an onshore field in southern Mexico. Two types of radioactive tracers were injected (Co60 and Co57); as well as a chemical tracer Ethyl Acetate (known as a primary tracer), which, through a hydrolysis reaction in the porous medium, produced the compounds Ethanol and Acetic Acid, the first being known as a secondary tracer. The production time of the test was 101 hours, and the samples were taken every 30 minutes continuously, accumulating a total of 202 samples from well 1011, received by the chemical tracers team. This work was carried out by a team made up of two groups of five specialists in each, to achieve continuous analysis (day and night). In each 12-hour shift, an average of 12 samples were analyzed, making a total of 202 samples of production fluid from the well under study on the location on the wells #7 of the Field.

Additionally, the concentration of the two radioactive tracers Co60 and Co57 was quantified with the on-line Measurement System for radioactive tracers at the head of oil wells, on-line and in real time, simultaneously with the well production. The data of the measured concentrations were transmitted wirelessly to the Mobile System (Section A of FIG. 1), located on the location on the wells #7 corresponding to the well under study, among the other 5 wells in the field.

Tables 2 and 3 show a summary of activities and samples analyzed at each stage of the analysis.

Figure 7:
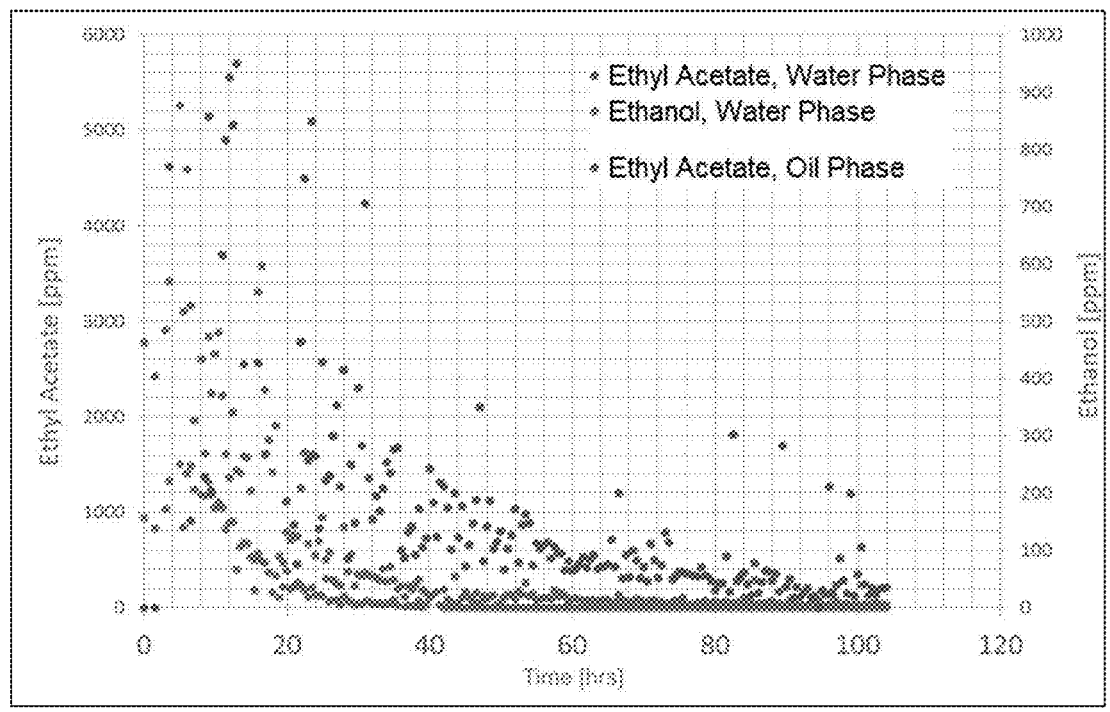
FIG. 7 shows the response unit curves vs. acquisition time, recorded by the gas chromatograph for both ethyl acetate and ethanol.
Figure 8:
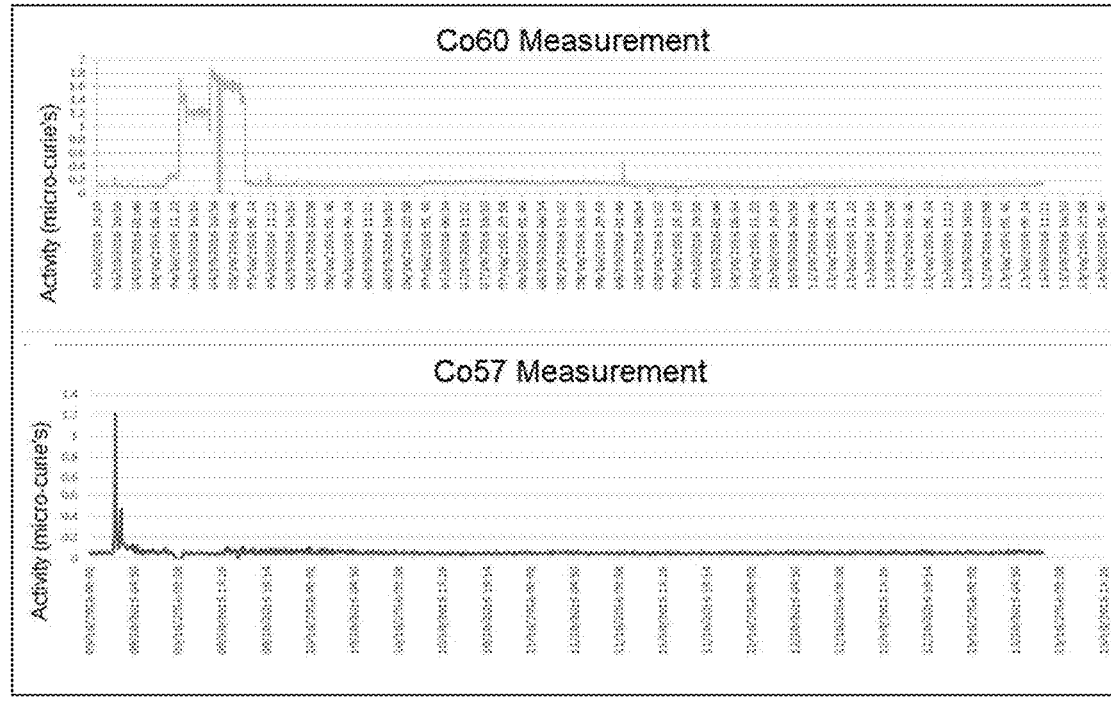
FIG. 8 shows the response curves obtained in the on-line measurement system of radioactive tracers at the head of oil wells, section A.

The graphs corresponding to the concentrations vs time resulting from the chromatographic analysis of the chemical tracers, ethyl acetate and ethanol, are presented in FIG. 7, which were obtained through the software developed with the chromatographic data of the corresponding components, in the computer located in section B point 16 of FIG. 1 of the Mobile System. Every hour, the points were added to the graph of FIG. 7, the corresponding data from the four extractions of process B. Also, the graph corresponding to the concentrations quantified with the radioactive tracers on-line measurement system and transmitted wirelessly to the receiving equipment located in section A, point 3 of the Mobile System, with the software developed for it, was formed, point by point every three minutes during the 11.74 days that the entire test lasted. The resulting graph is shown in FIG. 8. The measurement capacity of this system is highlighted, since previously, without this equipment, fewer samples (occupationally exposed personnel) were taken and sent for radiochemical analysis, in laboratories located in another city and even country where the test was being performed, and hence with the consequent loss of sensitivity in the results and very little information obtained, given the number of samples collected. (In addition to shipment complexity, the samples could not be sent individually, reason why a certain number of samples were packed to the laboratory).

Likewise, in terms of chemical tracers, the measurement at the well location and in real time is highlighted, with an hour lag, which means a huge advantage over what currently exists, since in conventional tests, acquired samples are sent to the laboratory for analysis, often located far from the oil field area, and even outside the country for analysis, which most likely implies degradation of the sample and the waiting time to obtain lab results.

In summary, the present invention represents in itself an important advantage over conventional methods, given the sensitivity of the results, their reliability, as well as the short times of the tests. Additionally, it is mentioned that with this on-line and real-time monitoring system, it is possible to design tracer tests with more ambitious objectives, given the capacity and versatility of the invention (radioactive and chemical tracers, measured at the well location and in real time, measuring continuously, without interruption, for as long as the test requires), which until now did not exist. This is a very powerful tool for those who perform tracers tests in reservoirs.

TABLE 1

First ramp: 40° C. for 1 min.
Second ramp: rise 1° C./min up to 45° C. hold 1 min.

| Parameter | Value |
|---|---|
| Injection mode | Split |
| Injection volume | 1 µL |
| Capillary Column | DB-WAX |
| Capillary Column Lenght | 30 m |
| Capillary Column Diameter | 0.250 mm |
| Temperature Range | 20° C.-260° C. |
| Minimum oven temperature | 40° C. |

TABLE 1-continued

First ramp: 40° C. for 1 min.
Second ramp: rise 1° C./min up to 45° C. hold 1 min.

| Parameter | Value |
|---|---|
| Maximum oven temperature | 200° C. |
| Heating ramps | 2 |
| Injector temperature | 150° C. |
| Detector temperature | 300° C. |

TABLE 2

Analysis of chemical tracers.

| Stage | Total samples analyzed | Place of analysis | Observations |
|---|---|---|---|
| Before sampling | 24 | Terrestrial Field under study of the Southern Zone of | 16 correspond to the cleaning of the capillary column and calibration curves. 6 injection water samples taken from the three storage tanks. 2 corresponding to reaction kinetics. |
| During sampling | 204 | Mexico on the location of the wells | 101 corresponding to continuous sampling every 30 min in well 1011 and 3 samples from different wells (one sample from well SG-90 and two from well SG-110). |

TABLE 3

On-line measurement system for radioactive tracers at the head of oil wells.

| | |
|---|---|
| Operating time on detection of Co60 and Co57 | 19:14:53 from 1 Oct. 2015 to 13:05:40 on 13 Oct. 2016 (11.74 days) |
| Acquisition time | 1 minute |
| Rest time | 2 minutes |
| Total acquired data | 16913 |
| Total acquired data Co57 | 5610 |
| Total acquired data Co60 | 5610 |
| Total acquired data Ir192 | 5609 |
| Co57 erroneous data | 30 data |
| Co60 erroneous data | 28 data |
| Ir192 erroneous data | 29 data |
| Data acquisition effectiveness | 99.48%, 0.0051 error |

The invention claimed is:

1. A mobile system for radiochemical analysis of radioactive tracers and chromatographic analysis of chemical tracers, in situ and in real time, comprising:
a first section A comprising one or more radioactive tracers and equipment for radiochemical analysis of radioactive tracers;
a second section B comprising one or more chemical tracers and equipment for chromatographic analysis of chemical tracers;
wherein the first section A and the second section B are located in a motor vehicle which is joined to a trailer.

2. The system according to claim 1, wherein the first section A comprises the following equipment: a computer room which includes computer equipment and software designed to carry out an analysis of results obtained from radioactive tracers in a well; an on-line measurement system for the radioactive tracers in the well; equipment used to obtain pertinent data from the radioactive tracers in the well; an oscilloscope and electronic equipment used for the analysis; and wireless communication equipment for receiving information from the radioactive tracers and sending the information to the computer equipment for analysis.

3. The system, according to claim 1, wherein the second section B comprises the following equipment: a fume extraction hood, support equipment to carry out ventilation of unwanted gases; support centrifuges for phase separation; an emergency shower for personnel; a sink: gas cylinders for analysis of the one or more chemical tracers; and a chromatograph to perform component analysis on sample fluids.

4. The system according to claim 1, wherein the mobile system decreases a time needed to produce a sequence of sample values in situ relative to a stationary laboratory.

5. The system according to claim 1 wherein the system considers results prepared during the in situ testing and in real time.

6. The system according to claim 1 further comprising an on-line measurement system of radioactive tracers at ahead of an oil well that measures a concentration in a discharge line of the well in real time.

7. A process for the radiochemical analysis of radioactive tracers and chromatographic analysis of chemical tracers, in situ and in real time, wherein the process comprises:
a first subprocess A for analyzing one or more radioactive tracers performed in a first section A comprising equipment for radiochemical analysis of radioactive tracers; and
a second subprocess B for analyzing one or more chemical tracers performed in a second section B comprising one or more chemical tracers and equipment for chromatographic analysis of chemical tracers;
wherein the first section A and the second section B are located in a motor vehicle which is joined to a trailer.

8. The process according to claim 7, wherein the first subprocess A comprises the following steps: A.I. assembling a system for on-line measurement of radioactive tracers at the head of an oil well; A. II. installing the on-line measurement system in the oil well; A.III. verifying operating pressures of the on-line measurement system of the radioactive tracers at the head of the oil well; A. IV. starting up and configuring the on-line measurement system of radioactive tracers at the head of the oil well; implementing testing of information being transferred; scheduling the on-line measurement system according to the test design and commissioning the on-line measurement system before the injection of tracers: A.V. monitoring measurements taken by the on-line measurement system, in situ and in real time, and; A.VI. disassembling the on-line measurement system at the head of the oil well.

9. The process according to claim 7, wherein the second subprocess B comprises of the following steps: B.I. taking a sample and receiving it in a laboratory; B. II. pouring an amount of the sample required for the analysis of one or more chemical tracers into a cylinder, ordering the required amount of the sample together with a remaining amount of the sample, and selecting a centrifuge for phase separation; B.III. storing the sample; B. IV. processing the required amount of the sample in the centrifuge: B. IV. a. performing a liquid-liquid extraction on an aqueous inorganic phase of the centrifuged sample, B. IV. b. performing a liquid-liquid extraction on an organic phase of the centrifuged sample; and B.V. detecting and quantifiying the chemical tracers.

10. The process according to claim 7, wherein results of the analysis are verified using a mass balance as part of the real-time measurement.

11. The process according to claim 7, further comprising the step of incorporating results to the analysis in an automated way in an online system, including a chromatogram of each compound of interest.

12. The process according to claim 7, the second subprocess B further comprises an extraction of an aqueous inorganic phase, an extraction of an organic phase, and a chromatographic analysis of the extractions.

* * * * *